United States Patent

Möckli

Patent Number: 5,888,252
Date of Patent: Mar. 30, 1999

[54] PROCESSES FOR DYEING KERATIN-CONTAINING FIBRES WITH CATIONICAZO DYES

[75] Inventor: Peter Möckli, Schönenbuch, Switzerland

[73] Assignee: Ciba Specialty Chemicals Corporation, Tarrytown, N.Y.

[21] Appl. No.: 804,307

[22] Filed: Feb. 21, 1997

Related U.S. Application Data

[63] Continuation of Ser. No. 495,531, Jul. 28, 1995, abandoned.

[30] Foreign Application Priority Data

Nov. 30, 1993 [CH] Switzerland ............... 3568/93

[51] Int. Cl.$^6$ .................................................. A61K 7/13
[52] U.S. Cl. .................... 8/426; 8/404; 8/405; 8/569; 8/571; 8/573; 8/655
[58] Field of Search ............... 8/404, 405, 423, 8/426, 428, 429, 567, 568, 569, 571, 573, 638, 639, 654, 655, 657, 666, 670, 689, 691, 916, 917, 572, 575, 576, 659, 692

[56] References Cited

U.S. PATENT DOCUMENTS

| | | | |
|---|---|---|---|
| 3,330,617 | 7/1967 | Lewis | 8/655 |
| 3,869,454 | 3/1975 | Lang et al. | 260/244 R |
| 4,025,301 | 5/1977 | Lang et al. | 8/10.1 |
| 4,151,162 | 4/1979 | Lang et al. | 260/158 |
| 4,168,144 | 9/1979 | Curry et al. | 8/426 |
| 5,474,578 | 12/1995 | Chan et al. | 8/431 |

FOREIGN PATENT DOCUMENTS

| | | |
|---|---|---|
| 3829870 | 4/1989 | Germany . |
| 4137005 | 5/1993 | Germany . |

OTHER PUBLICATIONS

Chem. Abst. 112: 145333b—DE 3,829,870A1, Apr. 1989.

*Primary Examiner*—Paul Lieberman
*Assistant Examiner*—Caroline D. Liott
*Attorney, Agent, or Firm*—Kevin T. Mansfield

[57] ABSTRACT

A process for dyeing keratin-containing fibers, comprises treating said fibers with a tinctorially effective amount of a dye of the formula

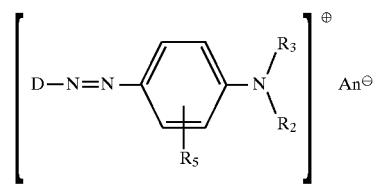

where D is the radical of a diazo component of the formula

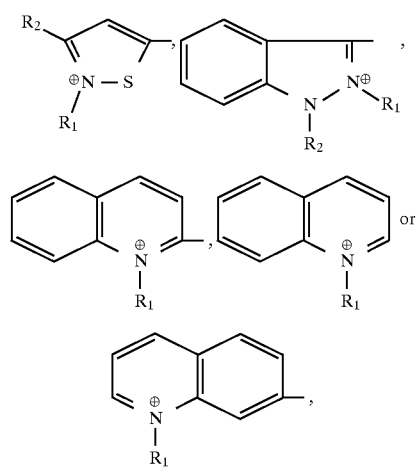

$R_1$ is an unsubstituted $C_1$–$C_4$alkyl, or $C_1$–$C_4$alkyl substituted with OH, $C_1$–$C_4$alkoxy, halogen, CN, amino, $C_1$–$C_4$monoalkylamino, or di-$C_1$–$C_4$alkylamino, $R_2$ and $R_3$ are independently of each other hydrogen, an unsubstituted $C_1$–$C_4$alkyl, or $C_1$–$C_4$alkyl substituted with OH, $C_1$–$C_4$alkoxy, halogen, CN, amino, $C_1$–$C_4$monoalkylamino, or di-$C_1$–$C_4$alkylamino, or $R_3$ and $R_2$, together with the nitrogen and carbon atoms joining them together form a 5- or 6-membered ring, $R_5$ is hydrogen, $C_1$–$C_4$alkoxy, halogen, $C_1$–$C_4$alkyl or $C_1$–Calkylcarbonylamino, or $R_5$ and $R_2$, together with the nitrogen and carbon atoms joining them together form a 5- or 6-membered ring, and $An^\ominus$ is a colorless anion.

11 Claims, No Drawings

PROCESSES FOR DYEING KERATIN-CONTAINING FIBRES WITH CATIONIC AZO DYES

This is a continuation of application Ser. No. 08/495,531 filed Jul. 28, 1995, now abandoned.

The present invention relates to a process for dyeing keratin-containing fibres, in particular human hair, with cationic dyes.

By far the largest proportion of all hair dyeings are carried out, even today, using so-called "oxidation colours", which involves applying small, colourless precursor molecules to the hair and reacting them by an oxidation process to form larger, coloured molecules. Although this produces the most durable ("permanent") colourings, increasing reservations are being voiced about possible toxicological risks posed not only by the substances used as starting materials but also by the oxidation intermediate and end products, whose precise composition is virtually uncontrollable. Further disadvantages are the relatively complicated use and in particular also the hair damage due to the aggressive chemicals used.

The other, so-called "semipermanent" and "temporary" colourings involve the use of ready-prepared dyes, specifically primarily uncharged disperse dyes and relatively sparingly water-soluble acid dyes. Cationic dyes, by contrast, play only a very minor part. As the terms "semipermanent" and "temporary" indicate, these colourings only have a medium to poor fastness level. Especially the cationic dyes have a reputation for poor hydrolysis and light resistance and for uneven colouring of the hair, for example between root and tip (see: John F. Corbett: The Chemistry of Haircare Products, JSDC August 1976, p. 290). In addition, the known cationic dyes have an insufficient build-up; i.e., even if increased amounts are used, it is impossible to exceed a certain, relatively low, colour strength. For instance, it is not possible to achieve a deep black coloration with the most important cationic hair dyes Basic Yellow 57, Basic Red 76, Basic Blue 99, Basic Brown 16 and Basic Brown 17 which are used in practice. For the same reason it is difficult to tint relatively dark natural hair with these dyes.

It has now been found that surprisingly cationic dyes of the below-indicated formulae have none of these disadvantages. They can be used to achieve in a very simple way and under gentle conditions very deep dyeings having excellent light, shampooing and crock fastness properties. Owing to their extremely clean shades, they also extend the range of possible mixed shades considerably, especially in the direction of the increasingly important brilliant fashion colours. fastness properties. Owing to their extremely clean shades, they also extend the range of possible mixed shades considerably, especially in the direction of the increasingly important brilliant fashion colours.

The present invention accordingly provides a process for dyeing keratin-containing fibres, which comprises treating the fibres with a dye of the formula

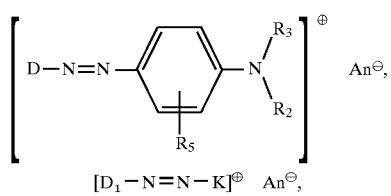

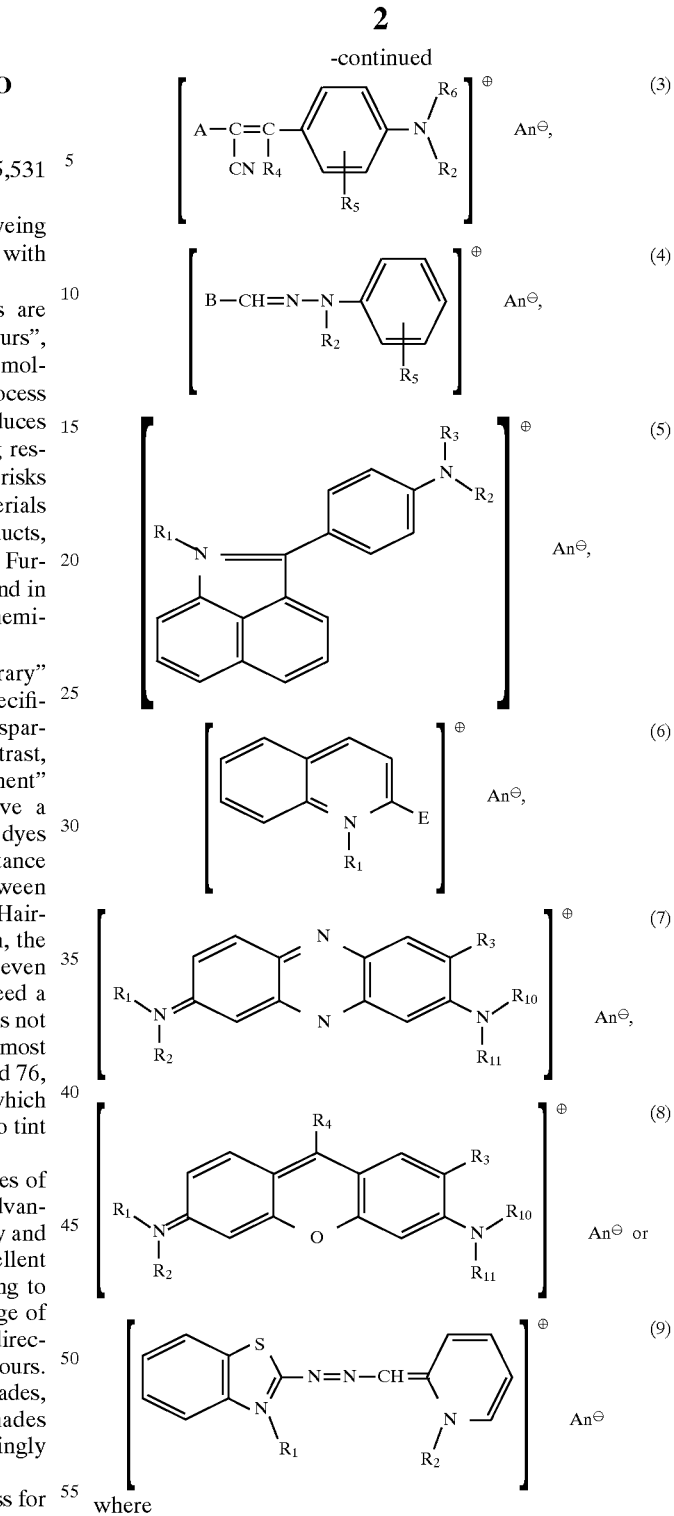

where

D is the radical of a diazo component of the formula

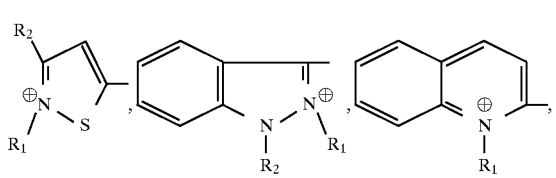

K is the radical of a coupling component of the formula with the proviso that either $D_1$ or K carries a cationic charge, $R_8$ is hydrogen, $C_1$–$C_4$alkyl, $C_1$–$C_4$alkoxy, halogen or amino, $R_9$ is hydroxyl or amino A is CN or tri-$C_1$–$C_4$alkylammonium-substituted $C_1$–$C_4$alkoxycarbonyl, B is a radical of the formula E is a radical of the formula $R_{10}$ and $R_{11}$ are independently of each other hydrogen or unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, or $R_{10}$ and $R_{11}$ are together with the nitrogen atom joining them together a 5- or 6-membered ring, and An$\ominus$ is a colourless anion.

For the purposes of the present invention, alkyl radicals are generally straight-chain or branched $C_1$–$C_4$alkyl groups. Suitable are for example methyl, ethyl, n-propyl, isopropyl, n-butyl, sec-butyl or tert-butyl.

Suitable alkoxy radicals are those having 1 to 4 carbon atoms, e.g. methoxy, ethoxy, propoxy, isopropoxy, n-butoxy, isobutoxy or tert-butoxy.

Halogen is to be understood as meaning fluorine, bromine, iodine or in particular chlorine.

If $R_5$ and $R_2$ are combined with the nitrogen atom and the two carbon atoms joining them together into a 5- or 6-membered ring, this ring may contain a further heteroatom, for example oxygen or sulfur. Moreover, the ring may be substituted, for example by hydroxyl, alkoxy, alkyl, halogen, CN or phenyl, or carry a further fused-on benzene ring. Preferred rings formed by $R_5$, $R_2$, the linking carbon atoms and the nitrogen atom are pyrroline, dihydrooxazine and di- or tetrahydropyridine rings carrying 0 to 4 methyl groups.

$R_2$ and $R_3$ can also combine with the nitrogen atom joining them together to form a piperidine, morpholine or piperazine radical. The piperazine radical can be substituted at the nitrogen atom which is not bonded to the phenyl ring by $C_1$–$C_4$alkyl or hydroxy-$C_1$–$C_4$alkyl or amino-$C_1$–$C_4$alkyl. The preferred substituent is hydroxyethyl.

—continued $R_1$ is unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, $R_2$ and $R_3$ are independently of each other hydrogen or unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, or $R_3$ and $R_2$ are together with the nitrogen atom joining them together a 5- or 6-membered ring, $R_4$ is hydrogen or CN, $R_5$ is hydrogen, $C_1$–$C_4$alkoxy, halogen, $C_1$–$C_4$alkyl or $C_1$–$C_4$alkylcarbonylamino, or $R_5$ and $R_2$ are together with the nitrogen and carbon atoms joining them together a 5- or 6-membered ring, $R_6$ is hydrogen or unsubstituted or OH—, $C_1$–$C_4$alkoxy-, halogen-, CN—, amino-, $C_1$–$C_4$monoalkylamino-, di-$C_1$–$C_4$alkylamino- or tri-$C_1$–$C_4$alkylammonium-substituted $C_1$–$C_4$alkyl, $R_7$ is hydrogen, unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl or $C_1$–$C_4$alkoxy, $D_1$ is the radical of a diazo component of the formula Suitable anions An⊖ include organic as well as inorganic anions, for example chloride, bromide, sulfate, hydrogen sulfate, methosulfate, phosphate, borotetrafluoride, carbonate, bicarbonate, oxalate, formate, acetate, propionate, lactate or complex anions, such as the anion of zinc chloride double salts.

The anion is generally given by the method of preparation. Preferred anions are chloride, sulfate, hydrogensulfate, methosulfate, phosphate, formate, acetate or lactate.

To dye by the process of the invention it is preferable to use a dye of the formula (1) or (2).

Of the dyes of the formula (1), particular preference is given to those where $R_1$ is unsubstituted $C_1$–$C_4$alkyl, especially methyl or ethyl.

Particular preference is also given to dyes of the formula (1) where $R_2$ and $R_3$ are independently of each other hydrogen or unsubstituted $C_1$–$C_4$alkyl, especially methyl or ethyl, and to those where $R_5$ is hydrogen, methoxy, ethoxy, chlorine, methyl or ethyl.

Of the dyes of the formula (1), particular preference is further given to those where D is the radical of a diazo component of the formula

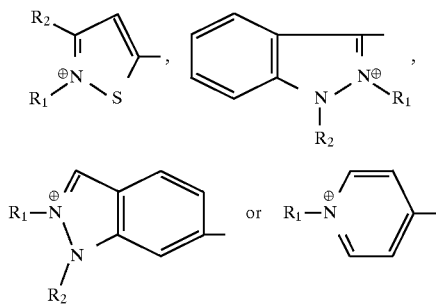

where $R_1$ is unsubstituted $C_1$–$C_4$alkyl, especially methyl or ethyl, and $R_2$ is hydrogen or unsubstituted $C_1$–$C_4$alkyl, especially methyl or ethyl.

Preferred dyes of the formula (2) are those where $D_1$ is the radical of a diazo component of the formula

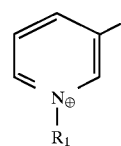

and K is the radical of a coupling component of the formula

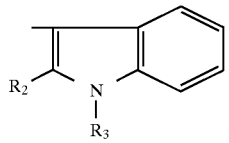

and those where $D_1$ is the radical of a diazo component of the formula

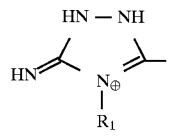

and K is the radical of a coupling component of the formula

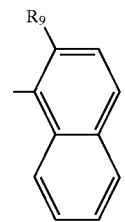

where $R_1$ is unsubstituted $C_1$–$C_4$alkyl, especially methyl or ethyl, $R_2$ and $R_3$ are independently of each other hydrogen or unsubstituted $C_1$–$C_4$alkyl, especially methyl or ethyl, and $R_9$ is hydroxyl or amino.

In the dyes of the formula (3), either the radical A or the radical $R_6$ has to carry a trialkylammonium group.

Preferred dyes of the formula (3) are those where A is CN, $R_5$ is hydrogen or unsubstituted $C_1$–$C_4$alkyl, especially methyl or ethyl, $R_2$ is unsubstituted $C_1$–$C_4$alkyl, especially methyl or ethyl, and $R_6$ is tri-$C_1$–$C_2$alkylammonium.

A trialkylammonium group A in the dyes of formula (3) is preferably a tri-$C_1$–$C_2$alkylammonium group. In such dyes, $R_2$ and $R_6$ are preferably independently of each other hydrogen or unsubstituted $C_1$–$C_4$alkyl, especially methyl or ethyl, and $R_5$ is preferably hydrogen, methoxy, ethoxy, chlorine, methyl or ethyl.

In preferred dyes of formula (4), $R_1$ is unsubstituted $C_1$–$C_4$alkyl, especially methyl or ethyl, and $R_2$ and $R_5$ are independently of each other hydrogen or unsubstituted $C_1$–$C_4$alkyl, especially methyl or ethyl.

Of the dyes of the formula (5), particular preference is given to those where $R_1$ is unsubstituted $C_1$–$C_4$alkyl, especially methyl or ethyl.

Particular preference is also given to the dyes of the formula (5) where $R_2$ and $R_3$ are independently of each other hydrogen or unsubstituted $C_1$–$C_4$alkyl, especially methyl or ethyl.

In a dye of formula (6), preferably $R_1$ is unsubstituted $C_1$–$C_4$alkyl, especially methyl or ethyl, and E is a radical of the formula

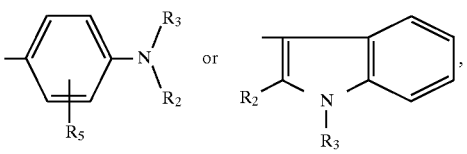

where $R_2$ and $R_3$ are independently of each other hydrogen or unsubstituted $C_1$–$C_4$alkyl, especially methyl or ethyl, and $R_5$ is hydrogen or unsubstituted $C_1$–$C_4$alkyl, especially hydrogen.

Of the dyes of the formula (7), preference is given to the use of those where $R_1$ is unsubstituted $C_1$–$C_4$alkyl, especially methyl or ethyl.

Particular preference is also given to dyes of the formula (7) where $R_2$ and $R_3$ are independently of each other hydrogen or unsubstituted $C_1$–$C_4$alkyl, especially methyl or ethyl, and $R_{10}$ and $R_{11}$ are each hydrogen.

In a dye of the formula (8), preferably $R_1$ is unsubstituted $C_1$–$C_4$alkyl, especially methyl or ethyl.

Particular preference is also given to dyes of the formula (8) where $R_2$, $R_3$, $R_{10}$ and $R_{11}$ are each independently of the others hydrogen or unsubstituted $C_1$–$C_4$alkyl, especially methyl or ethyl.

Of the dyes of the formula (9), preference is given to using those where $R_1$ and $R_2$ are each unsubstituted $C_1$–$C_4$alkyl, especially methyl or ethyl.

The dyes of the formulae (1) to (9) are known or can be prepared in a manner known per se.

The present invention further provides a process for dyeing keratin-containing fibres, which comprises treating the fibres with a mixture of at least two cationic dyes of the formulae (1) to (9).

Preference is given to using a mixture of at least three cationic dyes of the formulae (1) to (9) and in particular to a mixture of a yellow, a red and a blue cationic dye of the formulae (1) to (9).

The processes of the invention are suitable for dyeing furs and also animal and human hair, especially live human hair and domestic animals' hair. As a consequence of the high affinity and the good water solubility of the dyes used, it is possible to do the dyeing at room temperature from aqueous solutions without any assistants whatsoever.

However, it is also possible to use any customary cationic dye assistants used in the dyeing of hair, for example wetting agents, swelling agents, penetration aids or scents. In addition, the dyes can be incorporated into shampoos, creams, gels or pastes. Such cosmetic formulations for dyeing hair comprising at least one dye of the above-indicated formulae (1) to (6) and also assistants form a further part of the subject-matter of the present invention.

A particular advantage of the dyes used according to the invention for dyeing hair is that, owing to the good build-up of the dyes, the colourings can be prepared by the trichromatic principle; that is, it is possible by using a yellow, a red and a blue dye in suitable mixtures of these dyes to achieve virtually all shades. In addition, exact prediction of the shades obtained is possible, which is not the case with the so-called "oxidation dyes" owing to the varying composition of the end products.

Using colorimetric methods of measurement it is also possible to obtain on natural, unbleached hair predicted shades having regard to the hair's natural colour by determining its yellow, red and blue content and deducting it from the recipe of the desired shade. This is not feasible with the hair dyes previously used.

The colourings obtained are crock-, water-, wash- and light-fast and stable to permanent-deformation agents, for example thioglycolic acid.

The Examples which follow illustrate the invention. Parts and percentages are by weight. The temperatures are given in degrees Celsius.

EXAMPLE 1

A braid-sewn strand of blond, natural, untreated human hair is dyed at 25° C. for 5 minutes in a conventional manner with a dye emulsion containing 0.1% of the blue dye of the formula

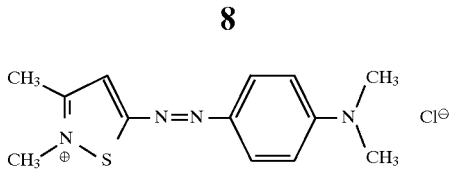

3.5% of Cetearyl Alcohol
1.0% of Ceteareth 80
0.5% of glyceryl mono-di-stearate
3.0% of stearamide DEA
1.0% of stearamphopropylsulfonate
0.5% of polyquaternium-6 and
water to 100%.

Then the hair is thoroughly rinsed with water and air-dried. The result is an intensive brilliant blue colouring. The light, shampooing and friction fastness properties of the colouring according to the invention are excellent.

EXAMPLE 2

Example 1 is repeated with the dye of the formula

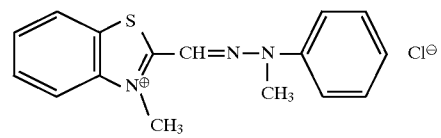

affording an intensively yellow colouring with likewise excellent fastness properties.

EXAMPLE 3

A 1% Solution of the dye of the formula

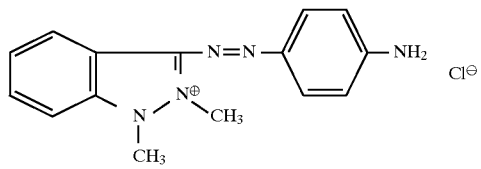

in a surfactant base containing 10% of cocoamphoglycinate and 90% of water is applied to Chinese, bleached yak hair at 25° C. for 5 minutes, and then the hair is thoroughly rinsed and air-dried. An intensively red colouring is obtained with good light fastness.

EXAMPLES 4–35

The method of Examples 1–3 is applied with the dyes listed below in the table, affording colourings on the hair in the specified hues.

| Example | Dye | Hue |
|---|---|---|
| 4 | | blue |

-continued
| Example | Dye | Hue |
|---|---|---|
| 5 | 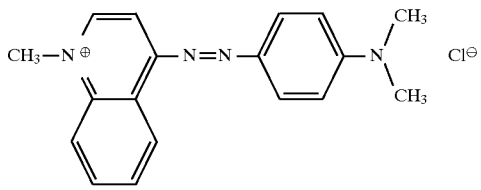 | blue |
| 6 | 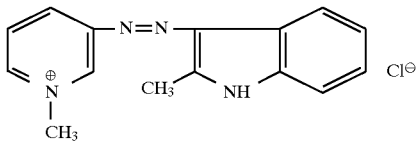 | yellow |
| 7 | 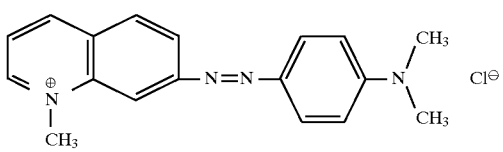 | orange |
| 8 | 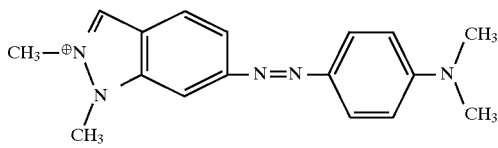 | reddish orange |
| 9 | 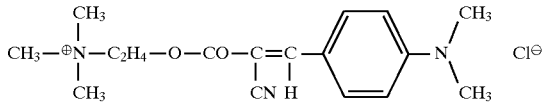 | yellow |
| 10 | 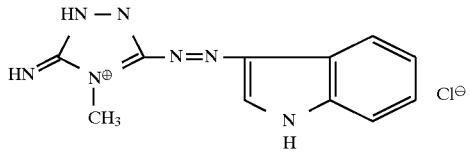 | reddish yellow |
| 11 | 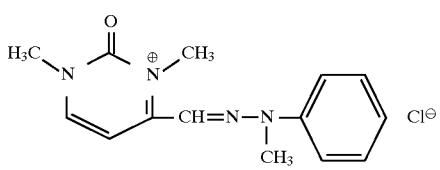 | yellow |
| 12 | 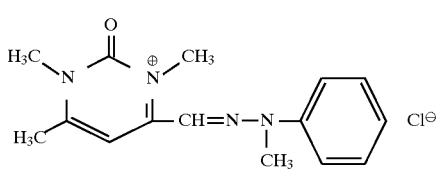 | yellow |
| 13 | 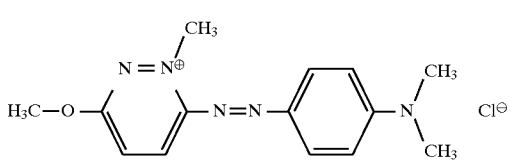 | reddish bluish violet |

-continued
| Example | Dye | Hue |
|---|---|---|
| 14 | 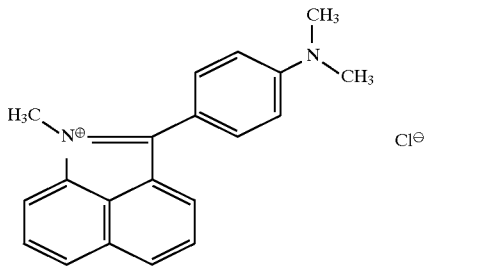 | bluish violet |
| 15 | 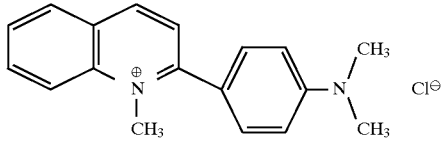 | orange |
| 16 | 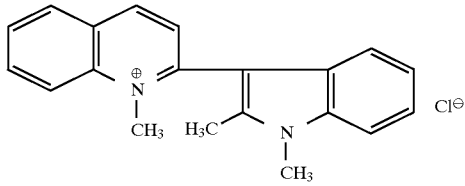 | yellow |
| 17 | 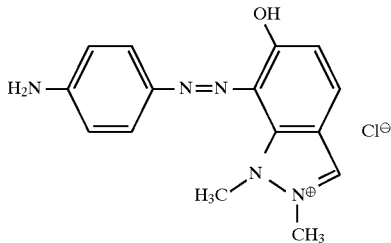 | brown |
| 18 | 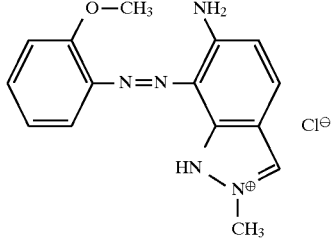 | red |
| 19 | 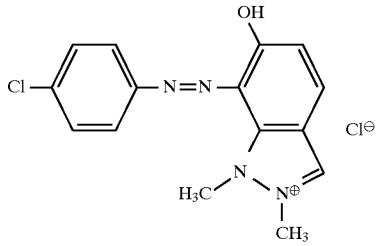 | yellow |
| 20 | 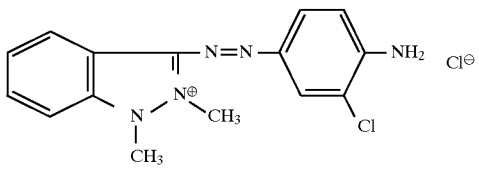 | scarlet |

-continued

| Example | Dye | Hue |
|---|---|---|
| 21 | (structure: indazole with N⁺(CH₃)₂, N=N linked to phenyl-N(CH₃)₂, Cl⁻) | violet |
| 22 | (NC)₂C=CH–C₆H₄–N(CH₃)–CH₂–CH₂–N⁺(CH₃)₃ Cl⁻ | yellow |
| 23 | (NC)₂C=C(CN)–C₆H₄–N(CH₃)–CH₂–CH₂–N⁺(CH₃)₃ Cl⁻ | red |
| 24 | (phenazine-type structure with =N⁺(CH₃)₂ and NH₂, NH, Cl⁻) | violet (neutral) |
| 25 | (phenazine-type structure with =N⁺(CH₃)₂, CH₃, NH₂, NH, Cl⁻) | red (neutral) |
| 26 | (xanthene structure with =N⁺(CH₃)₂ and N(CH₃)₂, O bridge, Cl⁻) | red |
| 27 | (xanthene structure with CN at 9-position, =N⁺(CH₃)₂ and N(CH₃)₂, O bridge, Cl⁻) | blue |
| 28 | (N-methylpyridinium–N=N–naphthol, Cl⁻) | yellow |
| 29 | (methoxy-methylpyridazinium–N=N–methoxyphenyl-N(CH₃)₂, Cl⁻) | red |

| Example | Dye | Hue |
|---|---|---|
| 30 | (structure) | red |
| 31 | (structure) | violet |
| 32 | (structure) | violet |
| 33 | (structure) | violet |
| 34 | (structure) | violet |
| 35 | (structure) | yellow |

What is claimed is:

1. A process for dyeing keratin-containing fibers, which comprises treating said fibers with a tinctorially effective amount of a dye of the formula

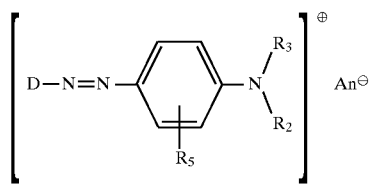

where D is the radical of a diazo component of the formula

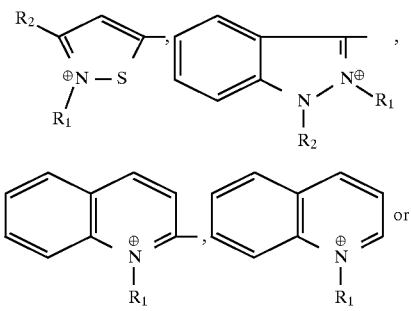
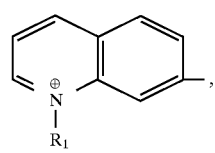

$R_1$ is an unsubstituted $C_1$–$C_4$alkyl, or $C_1$–$C_4$alkyl substituted with OH, $C_1$–$C_4$alkoxy, halogen, CN, amino, $C_1$–$C_4$monoalkylamino, or di-$C_1$–$C_4$alkylamino, $R_2$ and $R_3$ are independently of each other hydrogen, an unsubstituted $C_1$–$C_4$alkyl, or $C_1$–$C_4$alkyl substituted with OH, $C_1$–$C_4$alkoxy, halogen, CN, amino, $C_1$–$C_4$monoalkylamino, or di-$C_1$–$C_4$alkylamino, or $R_3$ and $R_2$, together with the nitrogen and carbon atoms joining them together form a 5- or 6-membered ring and $R_5$ is hydrogen, $C_1$–$C_4$alkoxy, halogen, $C_1$–$C_4$alkyl or $C_1$–$C_4$alkylcarbonylamino, or $R_5$ and $R_2$, together with the nitrogen and carbon atoms joining them together form a 5- or 6-membered ring, and $An^\ominus$ is a colorless anion.

2. A process according to claim 1, wherein $R_1$ and $R_2$ are, independently, methyl or ethyl.

3. A process according to claim 1, wherein the dye is of the formula (1) where $R_1$ is unsubstituted $C_1$–$C_4$alkyl.

4. A process according to claim 3, wherein $R_1$ is methyl or ethyl.

5. A process according to claim 1, wherein the dye is of the formula (1) where $R_5$ is hydrogen, methoxy, ethoxy, chlorine, methyl or ethyl.

6. A process according to claim 1, wherein

D is the radical of a diazo component of the formula

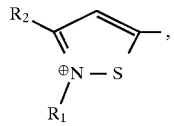

$R_1$ and $R_2$ are methyl, $R_5$ is hydrogen and $An^\ominus$ is a chloride ion.

7. A process according to claim 1, wherein

D is the radical of a diazo component of the formula

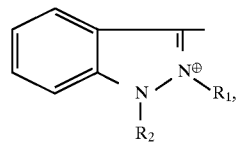

$R_1$, $R_2$ and $R_5$ are hydrogen and $An^\ominus$ is a chloride ion.

8. A process according to claim 1, wherein

D is the radical of a diazo component of the formula

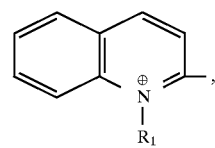

$R_1$ and $R_2$ are methyl, $R_5$ is hydrogen and $An^\ominus$ is a chloride ion.

9. A process according to claim 1, wherein

D is the radical of a diazo component of the formula

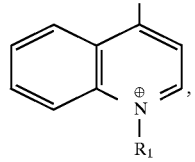

$R_1$ and $R_2$ are methyl, $R_5$ is hydrogen and $An^\ominus$ is a chloride ion.

10. A process according to claim 1 for dyeing live human hair.

11. A process according to claim 1 for dyeing hairs of domestic animals.

* * * * *